United States Patent [19]

Bryan et al.

[11] Patent Number: 5,726,034
[45] Date of Patent: Mar. 10, 1998

[54] AGLUCONE ISOFLAVONE ENRICHED VEGETABLE PROTEIN EXTRACT AND PROTEIN MATERIAL, AND HIGH GENISTEIN AND DAIDZEIN CONTENT MATERIALS AND PROCESS FOR PRODUCING THE SAME

[75] Inventors: Barbara A. Bryan, University City, Mo.; Maryann C. Allred, Collinsville, Ill.

[73] Assignee: Protein Technologies International, Inc., St. Louis, Mo.

[21] Appl. No.: 709,026

[22] Filed: Sep. 6, 1996

[51] Int. Cl.$^6$ .............. C21P 21/06; C12N 9/24; A61K 31/337; A61K 35/78
[52] U.S. Cl. .............. 435/68.1; 435/76; 435/125; 435/200; 435/272; 424/195.1; 252/398; 252/404; 252/407; 426/545; 426/546; 426/598; 426/634; 530/370; 530/378; 530/412; 530/414; 549/402; 549/403; 514/2; 514/456
[58] Field of Search .............. 435/68.1, 76, 200, 435/125, 272; 426/634, 545, 546, 598; 252/407, 404, 398; 424/195.1; 530/378, 370, 412, 414; 549/402, 403; 514/2, 456

[56] References Cited

U.S. PATENT DOCUMENTS

| | | | |
|---|---|---|---|
| 5,320,949 | 6/1994 | Shen | 252/407 |
| 5,351,384 | 10/1994 | Shen | 252/407 |
| 5,637,561 | 6/1997 | Shen et al. | 514/456 |
| 5,637,562 | 6/1997 | Shen et al. | 514/456 |

*Primary Examiner*—Herbert J. Lilling
*Attorney, Agent, or Firm*—Richard B. Taylor

[57] ABSTRACT

An aglucone is isoflavone enriched vegetable protein extract and protein material are provided, as well as a high genistein content material and a high daidzein content material. Isoflavone conjugates in a vegetable material are converted to isoflavone glucosides by treating the vegetable material at a temperature and a pH for a period of time sufficient to effect the conversion. The isoflavone glycosides are converted to glucose isoflavones by enzymatic reaction. The vegetable material is extracted with an aqueous extractant having a pH above about the isoelectric point of protein in the vegetable material to extract protein and the isoflavones either before or after conversion of the isoflavone conjugates to isoflavone glucosides or the conversion of the isoflavone glucosides to aglucone isoflavones. An aglucone isoflavone enriched protein material is produced by precipitating the protein and aglucone isoflavones from the extract. A high genistein content material or a high daidzein content material may be produced from the aglucone isoflavone enriched protein extract or aglucone isoflavone enriched protein material by separating the high genistein or high daidzein content material from the extract or protein material.

50 Claims, No Drawings

AGLUCONE ISOFLAVONE ENRICHED VEGETABLE PROTEIN EXTRACT AND PROTEIN MATERIAL, AND HIGH GENISTEIN AND DAIDZEIN CONTENT MATERIALS AND PROCESS FOR PRODUCING THE SAME

FIELD OF THE INVENTION

The present invention relates to an aglucone isoflavone enriched vegetable protein extract and protein material, and methods for providing such by performing a two-step process for converting isoflavone conjugates in a vegetable protein material to aglucone isoflavones, and to a high genistein content material and a high daidzein content material and methods for providing such from an aglucone isoflavone enriched protein material.

BACKGROUND OF THE INVENTION

Isoflavones occur in a variety of leguminous plants, including vegetable protein materials such as soybean. These compounds include daidzin, 6"-OAc daidzin, 6"-OMal daidzin, daidzein, genistin, 6"-OAc genistin, 6"-OMal genistin, genistein, glycitin, 6"-OAc-glycitin, 6"-OMal glycitin, glycitein, biochanin A, formononentin, and coumestrol. Typically these compounds are associated with the inherent, bitter flavor of soybeans.

The isoflavones in vegetable protein materials include isoflavone glucosides (glucones), isoflavone conjugates and aglucone isoflavones. Isoflavone glucosides have a glucose molecule attached to an isoflavone moiety. Isoflavone conjugates have additional moieties attached to the glucose molecule of an isoflavone glucoside, for example, 6"-OAc genistin contains an acetate group attached to the six position of the glucose molecule of genistin. Aglucone isoflavones consist solely of an isoflavone moiety.

Soy contains three "families" of isoflavone compounds having corresponding glucoside, conjugate, and aglucone members: the genistein family, the daidzein family, and the glycitein family. The genistein family includes the glucoside genistin; the conjugates 6"-OMal genistin (6"-malonate ester of genistin) and 6"-OAc genistin (6"-acetate ester of genistin); and the aglucone genistein. The daidzein family includes the glucoside daidzin; the conjugates 6"-OMal daidzin and 6"-OAc daidzin; and the aglucone daidzein. The glycitein family includes the glucoside glycitin; the conjugate 6"-OMal glycitin; and the aglucone glycitein.

In the production of commercial products, such as vegetable protein isolates and concentrates, the focus has been to remove these materials. For example, in a conventional process for the production of a soy protein isolate or concentrate in which soy flakes are extracted with an aqueous alkaline medium, much of the isoflavones are solubilized in the extract along with soy protein. The protein is precipitated from the extract by acidification of the extract and is separated to form an isolate or a concentrate, leaving a whey which retains much of the solubilized isoflavones. Residual isoflavones left in the acid precipitated protein are usually removed by exhaustive washing. The whey and the washes are typically discarded.

It has recently been recognized that the isoflavones contained in vegetable proteins such as soybeans have medicinal value. While all the isoflavones are of interest in medical evaluation, the aglucones are the specific isoflavones of most interest. Genistein and daidzein may significantly reduce cardivascular risk factors. "Plant and Mammalian Estrogen Effects on Plasma Lipids of Female Monkeys", *Circulation*, vol. 90, p. 1259 (October 1994). Genistein and daidzein are also thought to reduce the symptoms of conditions caused by reduced or altered levels of endogenous estrogen in women, such as menopause or premenstrual syndrome. Further, it has recently been recognized that aglucone isoflavones may inhibit the growth of human cancer cells, such as breast cancer cells and prostate cancer cells, as described in the following articles: "Genistein Inhibition of the Growth of Human Breast Cancer Cells, Independence from Estrogen Receptors and the Multi-Drug Resistance Gene" by Peterson and Barnes, *Biochemical and Biophysical Research, Communications*, Vol. 179, No. 1, pp. 661–667, Aug. 30, 1991; "Genistein and Biochanin A Inhibit the Growth of Human Prostrate Cancer Cells but not Epidermal Growth Factor Receptor Tyrosine Autophosphorylation" by Peterson and Barnes, *The Prostate*, Vol. 22, pp. 335–345 (1993); and "Soybeans Inhibit Mammary Tumors in Models of Breast Cancer" by Barnes, et al., *Mutagens and Carcinogens in the Diet*, pp. 239–253 (1990).

As noted above, the aglucone isoflavones include daidzein, genistein, and glycitein. These aglucones have the following general formula:

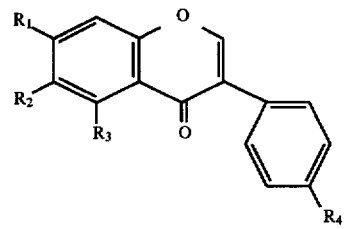

wherein, $R_1$, $R_2$, $R_3$ and $R_4$ may be selected from the group consisting of H, OH and $OCH_3$. Genistein has the formula above where $R_1$=OH, $R_2$=H, $R_3$=OH, and $R_4$=OH, daidzein has the formula above where $R_1$=OH, $R_2$=H, $R_3$=H, and $R_4$=OH, and glycitein has the formula above where $R_1$=OH, $R_2$=OCH_3$, $R_3$=H, and $R_4$=OH.

It is therefore to the aglucones and enrichment of a vegetable protein extract and a vegetable protein material with these compounds, and also to a high genistein content material and a high daidzein content material to which the present invention is directed. The present invention is also directed to methods of making an aglucone enriched vegetable protein extract, an aglucone isoflavone enriched vegetable protein material, a high genistein content material and a high daidzein content material.

A general process for converting vegetable protein isoflavone conjugates to aglucone isoflavones is known, and is provided in the currently pending application U.S. Ser. No. 08/477,102 filed Jun. 7, 1995 owned by the assignee of the present application.

Processes for converting glucosides to aglucone isoflavones are also known. A process for converting isoflavone glucosides to aglucone isoflavones to produce an aglucone isoflavone enriched vegetable protein extract and an aglucone isoflavone enriched vegetable protein isolate is provided in the currently pending PCT Patent Application No. PCT/US94/10697, owned by the assignee of the present invention.

Other process are also known in the art for converting isoflavone glucosides to aglucone isoflavones, such as described in Japanese Patent Application 258,669 to Obata, et al. Such processes do not provide for the conversion of isoflavone conjugates to aglucone isoflavones or provide a high genistein content material or a high daidzein content material derived from an aglucone enriched vegetable protein isolate. Furthermore, these processes achieve only a moderate extent of conversion of the glucosides to aglucones, and require a substantial period of time to effect this moderate extent conversion. Therefore, such processes are not desirable for large scale commercial operations.

It is therefore an object of the present invention to provide an aglucone isoflavone enriched vegetable protein extract and a process for producing the same.

It is further object of the present invention to provide an aglucone isoflavone enriched vegetable protein material, and a process for producing the same.

It is still a further object of the present invention to provide a high genistein content material and a high daidzein content material and processes for producing the same from an aglucone isoflavone enriched vegetable protein material.

SUMMARY OF THE INVENTION

The invention is an aglucone isoflavone enriched extract and a process for producing the same from a vegetable material containing isoflavone conjugates and protein. The process comprises extracting the vegetable material containing isoflavone conjugates with an aqueous extractant having a pH above about the isoelectric point of the protein in the vegetable material. The aqueous extract is treated at a temperature and pH for a time period sufficient to convert the isoflavone conjugates to isoflavone glucosides. An enzyme is contacted with the isoflavone glucosides in the aqueous extract at a temperature and a pH for a time period sufficient to convert the isoflavone glucosides to aglucone isoflavones, producing the aglucone isoflavone enriched extract.

In one embodiment of the invention, the extraction is carded out at a pH of from about 6 to about 10. Preferably the weight ratio of extractant to the vegetable protein material is from about 8:1 to about 16:1.

In another embodiment of the invention, the isoflavone conjugates are converted to isoflavone glucosides by treating the aqueous extract at a temperature of about 2° C. to about 121° C. and a pH value of about 6 to about 13.5. Preferably the conversion is effected a pH of about 11 and a temperature of about 5° C. to about 50° C., or, alternatively, at a pH of about 9 and a temperature of about 45° C. to about 75° C.

In yet another embodiment of the invention, the isoflavone glucosides are converted to aglucone isoflavones by contacting the isoflavone glucosides with an enzyme in the aqueous extract at a temperature between about 5° C. and about 75° C. and a pH value between about 3 and about 9. Preferably the enzyme is a saccharidase enzyme capable of cleaving 1,4-glucoside bonds.

In another embodiment of the invention, the pH of the aglucone isoflavone enriched extract is adjusted to about the isoelectric point of the protein in the extract to precipitate a protein material containing protein and aglucone isoflavones.

High conversion rates of isoflavone conjugates to isoflavone glucosides, and isoflavone glucosides to aglucone isoflavones are realized. In one embodiment, a majority, and preferably substantially all of the isoflavone conjugates are converted to aglucone isoflavones.

In another aspect, the invention is an aglucone isoflavone enriched protein material, and a process for producing the same from an isoflavone glucoside enriched protein material derived from a vegetable material containing isoflavone conjugates and protein. The vegetable material is extracted with an aqueous extractant having a pH above about the isoelectric point of the protein in the vegetable material. The aqueous extract is treated at a temperature and a pH for a time period sufficient to convert the isoflavone conjugates to isoflavone glucosides. A protein material containing isoflavone glucosides is separated from the extract, and the isoflavone glucosides in the protein material are contacted with an enzyme at a pH and a temperature for a time period sufficient to convert the isoflavone glucosides to aglucone isoflavones.

In still another aspect, the invention is an aglucone isoflavone enriched extract, and a process for producing the same from an isoflavone glucoside enriched vegetable material derived from a vegetable material containing isoflavone conjugates and protein. An aqueous slurry is formed of the vegetable material, and the slurry is treated at a pH and a temperature for a time period sufficient to convert the isoflavone conjugates to isoflavone glucosides. The isoflavone glucoside enriched vegetable material is then extracted with an aqueous extractant having a pH above about the isoelectric point of the protein in the vegetable material. The isoflavone glucosides in the extract are contacted with an enzyme at a temperature and a pH for a time period sufficient to convert the isoflavone glucosides to aglucone isoflavones.

In a preferred embodiment, the isoflavone glucosides in the extract are contacted with an enzyme by adding an effective mount of a supplemental enzyme to the extract, where the supplemental enzyme is preferably a saccharidase enzyme capable of cleaving 1,4-glucoside bonds.

In another embodiment, an aglucone isoflavone enriched protein material is formed from the aglucone isoflavone enriched extract by adjusting the pH of the extract to about the isoelectric point of the protein to precipitate a protein material containing protein and aglucone isoflavones.

In still another aspect, the invention is an aglucone isoflavone enriched protein material, and a process for producing the same from a protein material derived from a vegetable material containing isoflavone conjugates and protein. The vegetable material is extracted with an aqueous extractant having a pH above about the isoelectric point of the protein. A protein material containing isoflavone conjugates is separated from the extract by adjusting the pH of the extract to about the isoelectric point of the protein. An aqueous slurry is formed of the protein material, and the aqueous slurry is treated at a pH and a temperature for a period of time sufficient to convert the isoflavone conjugates to isoflavone glucosides. The isoflavone glucosides in the slurry are contacted with an enzyme at a pH and a temperature for a time period sufficient to convert the isoflavone glucosides to aglucone isoflavones.

In a preferred embodiment, the isoflavone glucosides in the slurry are contacted with an enzyme by adding an effective amount of a supplemental enzyme to the slurry, where the supplemental enzyme is preferably a saccharidase enzyme capable of cleaving 1,4-glucoside bonds.

In yet another aspect, the invention is a high genistein content material and a process for recovering the same from an aglucone isoflavone enriched vegetable protein material. An aglucone isoflavone enriched vegetable protein material is provided and is extracted with an aqueous alcohol extractant to produce an aglucone isoflavone enriched extract. The extract is contacted with an adsorbent material for a period of time sufficient to separate a high genistein content material from the extract.

In a final aspect, the invention is a high daidzein content material and a process for producing the same from an aglucone isoflavone enriched vegetable protein material. An aglucone isoflavone enriched vegetable protein material is provided and is extracted with an aqueous alcohol extractant to produce an aglucone isoflavone enriched extract. The extract is contacted with an adsorbent material for a period of time sufficient to separate a high daidzein content material from the extract.

DESCRIPTION OF THE PREFERRED EMBODIMENTS

The starting material of the preferred embodiment process is any vegetable protein material or plant material containing isoflavone conjugates and a vegetable protein. In a preferred embodiment, the starting material is a soybean material since the process is particularly suited for the production of aglucone isoflavone enriched extracts and protein materials from soybean material. The term "soybean material" as used herein refers to soybeans or any type of soybean derivative. The most preferred starting material is soybean flakes from which the oil has been removed by solvent extraction according to conventional procedures in the art. The present process is generally applicable to a wide array of vegetable protein materials besides soy or soybean materials.

Depending upon the type of vegetable plant material containing the isoflavone conjugates, it may be necessary in some instances to process the plant material into a finely divided form. This may be desirable to render the isoflavone compounds contained in the vegetable material accessible to the various reagents as described in greater detail below. The material may be ground, crushed, or otherwise processed by conventional methods known in the art. If the plant material is in a state such that the isoflavone compounds in the plant material are readily accessible to external reagents or reactants, such as small leafy portions of certain plants, it may not be necessary to subject the plant material to such processing.

In a first step or operation, vegetable protein and isoflavone compounds including isoflavone conjugates are extracted from the vegetable protein material. The flakes are extracted with an aqueous extractant having a pH above about the isoelectric point of the protein material, preferably at a pH of about 6.0 to about 10.0, and most preferably at a pH of about 6.7 to about 9.7. Typically alkaline reagents such as sodium hydroxide, potassium hydroxide, and calcium hydroxide may be employed, if needed, to elevate the pH of the aqueous extractant. The desired isoflavone compounds and vegetable proteins are solubilized in the aqueous extract.

It is preferred, to maximize recovery of the these compounds in the aqueous extract, that the weight ratio of soybean flakes or other vegetable protein material to extractant is controlled to specific levels to solubilize as much of the isoflavones in the vegetable material as possible. Extraction of the proteins and isoflavones can be carried out by conventional extraction procedures including countercurrent extraction of the vegetable protein material, preferably at a weight ratio of aqueous extractant to vegetable protein material from about 8:1 to about 16:1. Upon extracting the vegetable protein material, the extractant provides an aqueous extract of protein and isoflavones.

Alternatively, a two-step extraction process can be used, where preferably the weight ratio of extractant to vegetable protein material in an initial extraction is about 10:1, and the weight ratio of extractant to vegetable protein material in a second extraction is about 6:1, or less, so that the combined weight ratio of extractant to vegetable protein material in both extractions does not exceed a total weight ratio of extractant to vegetable protein material of about 16:1. Other extraction procedures may also be used in which the weight ratio of extractant to vegetable protein material is preferably 16:1 or less.

In a first isoflavone conversion step or operation, isoflavone conjugates in the aqueous extract are converted to isoflavone glucosides to produce an isoflavone glucoside enriched extract. The conversion has been found to be dependent on the pH and the temperature of the aqueous extract.

The pH range for conversion of the isoflavone conjugates to isoflavone glucosides is from about 6 to about 13.5. The pH of the aqueous extract should be adjusted to the desired pH, if necessary, with a suitable base, caustic agent, or basic reagent if the pH is to be raised, or, if the pH is to be lowered, with a suitable acid or acid reagent. The conversion of isoflavone conjugates to isoflavone glucosides has been found to be base catalyzed, and so it is most preferred to utilize a high pH to achieve rapid conversion. The most preferred pH for conversion of the isoflavone conjugates to isoflavone glucosides is a pH of about 9 to about 11.

The temperature range for conversion of the isoflavone conjugates to isoflavone glucosides is from about 2° C. to about 121° C. The temperature range at which the conversion readily occurs depends upon the pH of the aqueous extract. The inventors have found that the conversion occurs easily at a lower temperatures when the pH is relatively high. For example, at a pH of about 11 the conversion occurs rapidly and efficiently at a temperature range of about 5° C. to about 50° C. At a pH of about 9 conversion occurs efficiently within a temperature range of about 45° C. to about 75° C. When the pH of the aqueous extract is relatively low, the conversion occurs at higher temperatures. For example, at a pH of about 6, the conversion occurs within a temperature range of about 80° C. to about 121° C. In a preferred embodiment, the conversion is effected at about 35° C. and a pH of about 11. In another preferred embodiment, the conversion is effected at a temperature of about 73° C. and a pH of about 9.

The time period required for conversion of isoflavone conjugates to isoflavone glucosides in the first step depends primarily upon the pH and temperature range utilized. Such conversion times typically range from about 15 minutes up to several hours or longer. Conversion occurs more rapidly at a higher pH and at a higher temperature. At a pH of about 9, conversion is substantially complete in about 4 hours to about 6 hours at 73° C. In a most preferred embodiment, the isoflavone conjugates are converted to isoflavone glucosides in about 30 minutes to about 1 hour, preferably about 45 minutes, at a pH of about 11 and at a temperature of about 35° C.

The first conversion step is preferably performed in an aqueous system. Other water compatible components may be present in the system as well, such as low molecular weight alcohol, and other water soluble solvents.

The first isoflavone conversion step is remarkably efficient, converting at least a majority and preferably substantially all of the isoflavone conjugates to isoflavone glucosides. Typically from about 80% to about 100% of the isoflavone conjugates are converted to isoflavone glucosides. By use of the preferred reaction parameters previously described it is possible to achieve conversions of 95% or more. These high conversion rates are particularly attractive for large scale commercial operations.

In a second isoflavone conversion step or operation, the isoflavone glucosides produced in the first conversion step, as well as isoflavone glucosides previously resident in the aqueous extract, are converted to aglucone isoflavones by enzymatic reaction. The conversion produces an aglucone isoflavone enriched extract from the isoflavone glucoside enriched extract.

The second conversion step has been found to be dependent on the concentration of enzymes present in the extract, and their characteristics. The enzymes required to effect the conversion are enzymes capable of cleaving the glucosidic linkage between the isoflavone moiety and the glucose molecule of the isoflavone glucosides. In a preferred embodiment, the enzymes are saccharidase, esterase, or gluco-amylase enzymes capable of cleaving 1,4-glucoside bonds.

The concentration of enzymes required to convert the isoflavone glucosides to aglucone isoflavones is dependent on a variety of factors including the type of enzymes present in the aqueous extract, distribution of enzyme concentrations, activities of the enzymes, and the pH and temperature of the extract during the conversion. The enzymes may be inherently present in the extract either from the vegetable protein material or from microbial growth in the extract. Such inherently present enzymes are referred to herein as "residual" enzymes, and enzymes that are added to the extract are referred to herein as "supplemental" enzymes.

Sufficient enzyme should be present in the extract to convert at least a majority, and preferably substantially all, of the isoflavone glucosides to aglucone isoflavones. Generally, if the residual enzymes in the extract are insufficient to effect the conversion, supplemental enzymes should be added to the extract. In a preferred embodiment, supplemental enzymes are added to the extract regardless whether sufficient residual enzymes are present in the extract since addition of supplemental enzymes dramatically decreases the time necessary to effect substantially complete conversion of the glucosides to aglucones. If supplemental enzymes are added, the supplemental enzymes should be added so that the total concentration of enzyme present is about 0.1% to about 10% by weight of the vegetable protein material on a dry basis.

Supplemental enzymes are selected based on optimum activity at selected pH and temperature conditions, and cost effectiveness. The supplemental enzymes are enzymes capable of cleaving the bond between the isoflavone moiety and the glucose molecule of the isoflavone glucosides, such as saccharidase, esterase, and gluco-amylase enzymes capable of cleaving 1,4-glucoside bonds. Preferred supplemental enzymes are commercially available alpha-and beta-glucosidase enzymes, beta-galactosidase enzymes, gluco-amylase enzymes, and pectinase enzymes. Particularly preferred are enzymes such as Biopectinase 100L (which is preferably utilized at a pH range of from about 3 to about 6), Biopectinase 300L (optimum pH range from about 3 to about 6), Biopectinase OK 70L (optimum pH range from about 3 to about 6), Biolactase 30,000 (optimum pH range from about 3 to about 6) Neutral Lactase (optimum pH range from about 6 to about 8), all of which are available from Quest International, 1833 57th Street, Post Office Box 3917, Sarasota, Fla. 34243. Also especially preferred are Lactase F (which is preferably utilized at a pH range of from about 4 to about 6), and Lactase 50,000 (optimum pH range from about 4 to about 6), both available from Amano International Enzyme Co., Inc., Post Office Box 1000, Troy, Va. 22974. Other particularly preferred supplemental enzymes include G-Zyme G990 (optimum pH from about 4 to about 6) and Enzeco Fungal Lactase Concentrate (optimum pH from about 4 to about 6) available from Enzyme Development Corporation, 2 Penn Plaza, Suite 2439, New York, N.Y. 10121; Lactozyme 3000L (which preferably is utilized at a pH range from about 6 to about 8), and Alpha-Gal 600L (which preferably is utilized at a pH range of from about 4 to about 6.5), available from Novo Nordisk Bioindustrials, Inc., 33 Turner Road, Danbury, Conn. 06813; Maxilact L2000 (which is preferably utilized at a pH range of from about 4 to about 6), available from Gist Brocades Food Ingredients, Inc., King of Prussia, Pa., 19406; and Neutral Lactase (which is preferably utilized at a pH range of from about 6 to about 8), available from Pfizer Food Science Group, 205 East 42nd Street, New York, N.Y. 10017.

The pH range for conversion of the isoflavone glucosides to aglucone isoflavones is from about 3 to about 9. The pH that is utilized depends primarily upon the type of enzyme used, and should be selected accordingly. The residual enzyme is active within a pH range of about 7 to about 9, although it is believed that the pH of the extract is lowered during the course of the conversion. The supplemental enzymes are active within an optimum pH range specified by the manufacturer of the enzyme, as shown above for several specific enzymes. Typically the supplemental enzymes are active either in a neutral pH range from about 6 to about 8, or in an acidic pH range from about 3 to about 6.

The pH may be adjusted to a desired value for conducting the second isoflavone conversion step. In most instances the pH is reduced from the relatively high or basic pH of the first isoflavone conversion step by the addition of one or more suitable acids such as acetic acid, sulfuric acid, phosphoric acid, hydrochloric acid or any other suitable reagent.

The temperature range for the second isoflavone conversion step is from about 5° C. to about 75° C. The temperature significantly affects the activity of the enzymes, and therefore, the rate of conversion. The supplemental enzymes may be active above 70° C., for example Alpha-Gal 600L is active at 75° C., however, it is preferred to conduct the conversion at lower temperatures to avoid enzyme deactivation. In preferred embodiment, the conversion is effected between about 35° C. and about 45° C.

The time required for the second isoflavone conversion step depends upon enzyme-related factors, particularly concentration, and the temperature and pH of the system. In most instances it is possible to achieve substantially complete conversion within 24 hours, however, it is preferred that supplemental enzyme be added to dramatically increase the rate of the reaction. The selected supplemental enzyme, enzyme concentration, pH and temperature preferably cause substantially complete conversion within 2 hours, and most preferably within 1 hour.

The very high degrees of conversion with this process are such that at least a majority, and preferably substantially all, the isoflavone glucosides present in the extract, are converted to aglucone form. The term "a majority" refers to an extent of conversion of isoflavone glucosides to aglucone isoflavones of at least about 50%. The term "substantially all" refers to an extent of conversion of isoflavone glucosides to aglucone isoflavones of at least about 80%, and most preferably at least about 90%. Such high rates of conversion on a dependable basis are remarkable, and are desirable for commercial applications.

An aglucone isoflavone enriched protein material may be recovered from the aglucone isoflavone enriched extract. Upon completion of the second isoflavone conversion step, the pH is adjusted by the addition of acid, if necessary, to about the isoelectric point for the vegetable protein, for soy protein generally between about 4.0 to about 5.0 and preferably between about 4.4 to about 4.6. Protein is precipitated from the pH adjusted extract in the form of a curd. A significant portion of the aglucone isoflavones are captured in the curd. Following precipitation, the curd or precipitated protein is separated from the extract to form a protein material enriched with aglucone isoflavones. Preferably the aglucone isoflavone enriched protein material is separated from the extract by centrifugation or filtration.

In the most preferred embodiment, washing of the separated protein material is either avoided entirely or minimized in order to substantially reduce removal of the aglucone isoflavones from the protein material. Washing of the protein material with water may therefore be avoided completely, or be limited to a single washing with water during which the weight ratio of water to protein material is between about 2:1 to about 6:1. The lack of washing of the precipitated curd provides an protein material enriched with the desired levels of isoflavones, even though more extensive washing could be carried out with a lesser recovery of isoflavones.

The separated protein material may be dewatered by centrifugation or concentration or a combination thereof, and is dried in a conventional manner. The preferred embodiment is not intended to be limited by a particular means of dewatering, although it is preferred to use conventional dewatering and drying techniques such as centrifugation and spray drying to form a dried protein material.

The previously described preferred embodiment process utilizes both first and second isoflavone conversion steps immediately after obtaining an extract. The present invention also includes a process in which a vegetable material containing isoflavone conjugates and protein is extracted with an aqueous extractant having a pH above about the isoelectric point of the protein; the first isoflavone conversion step is performed on the extract; a protein material containing isoflavone glucosides is separated from the extract; and the second isoflavone conversion step is performed on the protein material. The steps in this process may be performed in the same general manner as described above.

The present invention further includes a process in which an aqueous slurry is formed of a vegetable material containing isoflavone conjugates and protein, the first isoflavone conversion step is performed on the aqueous slurry; the vegetable material is extracted with an aqueous extractant having a pH above about the isoelectric point of the protein; and the second isoflavone conversion step is performed on isoflavone glucosides in the extract. The aqueous slurry of vegetable material preferably contains up to 20% vegetable material by weight. The steps of this process may be performed in the same general manner as described above. Furthermore, a protein material containing aglucone isoflavones may be separated from the extract after the second isoflavone conversion step in the manner described above.

The present invention also includes a process in which a vegetable protein material containing isoflavone conjugates and protein is extracted with an aqueous extract having a pH above about the isoelectric point of the protein; a protein material containing isoflavone conjugates is separated from the extract; an aqueous slurry is formed of protein material; and the first and second isoflavone conversion steps are performed on the aqueous slurry of protein material. The aqueous slurry of protein material preferably contains up to 30% protein material by weight. The steps of this process may be performed in the same general manner as described above.

It is contemplated that both first and second isoflavone conversion steps could be performed upon an aqueous slurry of vegetable material containing isoflavone conjugates and protein, upon an extract of such a vegetable material, and upon a protein material separated from such an extract. The present invention includes combination of any of the foregoing steps to form an aglucone isoflavone enriched extract or protein material.

A high genistein content material and a high daidzein content material may be produced from the recovered aglucone isoflavone enriched protein material. As used herein, a high genistein content material is defined as a vegetable material containing at least 40% genistein, and most preferably at least 90% genistein, along with residual vegetable material, which is residual soy material if the high genistein content material is recovered from a soy material. A high daidzein content material contains at least 40% daidzein along with residual vegetable material, which is soy material if the high daidzein content material is recovered from a soy material.

The aglucone isoflavone enriched protein material may be initially washed and filtered to remove undesirable salts and sugars. The aglucone isoflavone enriched protein material is mixed with water where the water is present in up to a 6:1 ratio to the protein material. The water should be cold to minimize the solubility of the aglucone isoflavones in the water, and preferably has a temperature from about 5° C. to about 30° C. The protein material is mixed in the water for about 15 to about 30 minutes, and then the protein material is filtered from the water using any conventional filtering means, preferably filtering the mixture through conventional filter paper. The washing and filtering step may be avoided, if desired, to minimize any potential loss of aglucone isoflavones in the water wash.

The aglucone isoflavone enriched protein material may then be extracted with an aqueous alcohol extractant to remove the aglucone isoflavones from the protein material and produce an aglucone isoflavone extract. Low molecular weight alcohols such as methanol, and particularly ethanol, are preferred as the alcohol component of the extractant. The aglucone isoflavones have been found to be soluble at almost all alcohol concentrations of the extractant. The aglucone isoflavones are particularly soluble when the extractant contains between about 30% alcohol and about 90% alcohol, and most preferably the extractant contains between about 60% alcohol and about 80% alcohol. Although aqueous alcohol is the preferred solvent, other solvents including water, acetonitrile, methylene chloride, acetone, and ethyl acetate may be used to effect the extraction of the aglucone isoflavones from the protein material.

The extraction is carried out using a minimal mount of extractant. It is preferred that the weight ratio of extractant to the aglucone isoflavone enriched protein material not exceed 11:1. The extraction may be performed by any conventional extraction method, including countercurrent extraction, or a double extraction where the weight ratio of the combined extracts to the protein material does not exceed 11:1.

In a preferred embodiment, the protein material is initially extracted with 80% ethanol where the weight ratio of the extractant to protein material is about 6:1. The extractant is separated from the protein material by a conventional means for separation, such as a centrifuge or a filter press, and the extract is collected. The protein material is extracted again with 80% ethanol, where the weight ratio of the extractant to the protein material is about 4:1. The extractant is again collected and added to the initial collected extract. The protein material is then washed with a water flush, where the weight ratio of water to protein material is about 4:1, and the water is added to the collected extracts.

Although the extraction can be carried out at any pH, it is preferred that the extractant have a pH of about 7 to about 10. Protein gel formation is avoided within the preferred pH range, and, if the protein material is to be recovered as well as the aglucone isoflavone extract, formation of undesirable amino acid byproducts within the protein material is avoided within the preferred pH range.

The extraction can be carded out at any temperature up to the boiling point of the extractant, and preferably is conducted between about 25° C. and about 70° C. To effect the maximum removal of aglucone isoflavones from the protein material, it is preferred that the extraction be carried out at a temperature of about 50° C. to about 70° C., most preferably at about 60° C.

Following the extraction, a high genistein content material and a high daidzein content material may be separated from the aglucone isoflavone extract by contacting the extract with an adsorbent material for a time sufficient to separate the high genistein and high daidzein content materials from the extract. In a preferred embodiment, the high genistein and high daidzein content materials are separated from the extract by reverse phase High Performance Liquid Chromatography (HPLC). Genistein and daidzein are separated from other isoflavones and impurities in the extract by eluting the extract through particles of an adsorbent material which releasably binds the genistein, daidzein, other isoflavones, and impurities in a compound specific manner, thereby enabling each of the compounds to be separated.

The aglucone isoflavone extract is initially filtered to remove insoluble material that could plug an HPLC column. The extract may be filtered by any conventional filtering method. Most preferably the extract is filtered in a conventional ultrafiltration process which also removes residual protein that may be in the extract.

An HPLC column is prepared by packing a conventional commercially available HPLC column with a particulate adsorbent material which will releasably bind the genistein, daidzein, other isoflavones, and impurities in a compound specific manner. The adsorbent material may be any reverse phase HPLC packing material, however, a preferred packing material may be chosen by the criteria of load capacity, separation effectiveness, and cost. One such preferred packing material is Kromasil C18 16 μm 100 Å beads available from Eka Nobel, Nobel Industries, Sweden.

The filtered extract is passed through the packed HPLC column until all the binding sites of the column are fully saturated with isoflavones, which is detected by the appearance of isoflavones in the effluent from the column. The HPLC column may then be eluted with a polar eluent to effect the separation. In a preferred embodiment, the eluent is an aqueous alcohol. The aqueous alcohol eluent may have an alcohol content of between about 30% to about 90% alcohol, and preferably has an alcohol content of about 50% alcohol to provide both good separation and good solubility of the isoflavones. The alcohol is preferably methanol or ethanol, where ethanol is preferred when the high genistein or high daidzein content product materials are to be used in food or drug applications.

The high genistein and high daidzein content materials are collected from the column effluent. A fraction of effluent containing daidzein elutes from the column first, followed by a glycitein fraction, which is followed by the more polar genistein fraction. The daidzein and genistein fractions are collected as they elute from the column. The glycitein fraction may also be collected, if desired.

The alcohol in the fractions may be removed by evaporation, after which the high genistein and high daidzein content materials, and a high glycitein content material, can be recovered by conventional separation methods such as centrifugation or filtration. The recovered high genistein content material contains at least 40% genistein, and preferably at least 90% genistein, along with residual vegetable material, which is residual soy material if the genistein is recovered from a soy whey. The recovered high daidzein content material contains at least 40% daidzein, along with residual vegetable material.

EXPERIMENTAL

The present invention is illustrated in more detail by the following examples using a soy material as the vegetable material. The examples are intended to be illustrative, and should not be interpreted as limiting or otherwise restricting in scope of the invention in any way.

As noted above, soy material includes the genistein, daidzein, and glycitein "families" of isoflavones having corresponding glucoside, conjugate, and aglucone members, where the genistein family contains the conjugates 6'-OMal genistin and 6"-OAc genistin, the glucoside genistin, and the aglucone genistein; the daidzein family contains the conjugates 6"-OMal daidzin and 6"-OAc daidzin, the glucoside daidzin, and the aglucone daidzein; and the glycitein family contains the conjugate 6"-OMal glycitin, the glucoside glycitin, and the aglucone glycitein. In the following tables the relative concentrations of the isoflavones are measured as a percentage of a family of isoflavones. For example, in the genistein family: % genistin+% 6"-OMal genistin+% 6"-OAc genistin+% genistein=100%. The extent of conversion of conjugates to glucosides, and glucosides to aglucones can be determined by comparing the percentages of each type of compound in an isoflavone family.

EXAMPLE 1

In a first experiment, the conversion of isoflavone conjugates to isoflavone glucosides in a soy extract is examined. The extent of conversion is determined by the quantitative decrease of the percentage of malonate and acetate esters of an isoflavone family coupled with a corresponding quantitative increase of the percentage of the glucoside of the same isoflavone family.

A soy extract is prepared by slurrying 400 g of freely ground defatted soy flakes with 4000 g of water. The pH is adjusted to 9.7 with sodium hydroxide and the slurry is heated to 38° C. for 15 minutes with agitation. The slurry is then centrifuged and the extract is collected as supernatant.

The conversion of isoflavone conjugates to isoflavone glucosides is examined at different pH conditions and different temperatures. 600 g samples of the extract are adjusted to a pH of 6, 7, 9, and 11 with hydrochloric acid or sodium hydroxide. For each pH the 600 g sample is split into two 300 g samples, and these samples are incubated at 45° C. and 72.5° C. for 24 hours. Periodic analysis is conducted on each sample at 0, 2, 4, 6, and 24 hours to determine the isoflavone content of the samples. Table 1 below shows the change and distribution of isoflavones over the course of the experiment.

TABLE 1

| Sample | GEN-ISTIN | 6"-OMAL GENISTIN | 6"-OAC GENISTIN | GEN-ISTEIN | DAID-ZIN | 6"-OMAL DIADZIN | 6"-OAC DIADZIN | DAID-ZEIN | GLYCI-TIN | 6"-OMAL GLYCITIN | GLYCI-TEIN |
|---|---|---|---|---|---|---|---|---|---|---|---|
| | | | | | PERCENTAGES | | | | | | |
| pH 6, 45° C. | | | | | | | | | | | |
| t = 0 | 44 | 47 | 0 | 13 | 35 | 48 | 1 | 16 | 40 | 37 | 23 |
| t = 10 min | 42 | 49 | 0 | 9 | 39 | 49 | 1 | 11 | 41 | 37 | 22 |
| t = 2 hrs | 29 | 51 | 0 | 19 | 27 | 49 | 1 | 22 | 37 | 36 | 27 |
| t = 4 hrs | 25 | 50 | 0 | 25 | 22 | 49 | 1 | 28 | 36 | 35 | 29 |
| t = 6 hrs | 23 | 50 | 0 | 27 | 19 | 48 | 1 | 31 | 35 | 35 | 30 |
| t = 24 hrs | 15 | 43 | 1 | 40 | 12 | 42 | 0 | 46 | 30 | 32 | 37 |
| pH 7, 45° C. | | | | | | | | | | | |
| t = 0 | 44 | 47 | 0 | 13 | 35 | 48 | 1 | 16 | 40 | 37 | 23 |
| t = 10 min | 43 | 48 | 0 | 9 | 40 | 48 | 1 | 11 | 42 | 36 | 22 |
| t = 2 hrs | 38 | 48 | 0 | 13 | 35 | 48 | 1 | 16 | 40 | 37 | 23 |
| t = 4 hrs | 37 | 47 | 0 | 16 | 32 | 47 | 1 | 20 | 41 | 36 | 23 |
| t = 6 hrs | 36 | 46 | 0 | 18 | 31 | 46 | 1 | 22 | 41 | 35 | 24 |
| t = 24 hrs | 18 | 42 | 0 | 39 | 13 | 41 | 0 | 46 | 31 | 34 | 35 |
| pH 9, 45° C. | | | | | | | | | | | |
| t = 0 | 44 | 47 | 0 | 13 | 35 | 48 | 1 | 16 | 40 | 37 | 23 |
| t = 10 min | 46 | 46 | 0 | 8 | 43 | 46 | 1 | 10 | 45 | 33 | 23 |
| t = 2 hrs | 51 | 41 | 0 | 8 | 49 | 40 | 1 | 10 | 49 | 30 | 21 |
| t = 4 hrs | 57 | 36 | 0 | 7 | 54 | 35 | 1 | 10 | 52 | 27 | 21 |
| t = 6 hrs | 60 | 33 | 0 | 7 | 58 | 31 | 0 | 10 | 54 | 25 | 21 |
| t = 8 hrs | 58 | 26 | 0 | 15 | 55 | 25 | 0 | 20 | 50 | 23 | 27 |
| pH 11, 45° C. | | | | | | | | | | | |
| t = 0 | 44 | 47 | 0 | 13 | 35 | 48 | 1 | 16 | 40 | 37 | 23 |
| t = 10 min | 73 | 20 | 0 | 8 | 71 | 19 | 0 | 10 | 62 | 19 | 19 |
| t = 2 hrs | 92 | 0 | 0 | 7 | 91 | 0 | 0 | 9 | 82 | 0 | 18 |
| t = 4 hrs | 93 | 0 | 0 | 7 | 90 | 0 | 0 | 10 | 82 | 0 | 18 |
| t = 6 hrs | 93 | 0 | 0 | 7 | 90 | 0 | 0 | 10 | 81 | 0 | 19 |
| t = 24 hrs | 95 | 0 | 0 | 5 | 87 | 0 | 0 | 13 | 78 | 0 | 22 |
| pH 6, 72.5° C. | | | | | | | | | | | |
| t = 0 | 44 | 47 | 0 | 13 | 35 | 48 | 1 | 16 | 40 | 37 | 23 |
| t = 10 min | 42 | 48 | 0 | 9 | 40 | 48 | 1 | 12 | 40 | 35 | 24 |
| t = 2 hrs | 50 | 41 | 0 | 9 | 47 | 40 | 1 | 12 | 47 | 29 | 24 |
| t = 4 hrs | 56 | 34 | 0 | 9 | 53 | 34 | 1 | 12 | 52 | 23 | 24 |
| t = 6 hrs | 61 | 30 | 0 | 9 | 58 | 29 | 2 | 12 | 53 | 23 | 25 |
| t = 24 hrs | 84 | 7 | 0 | 9 | 80 | 6 | 2 | 12 | 66 | 5 | 29 |
| pH 7, 72.5° C. | | | | | | | | | | | |
| t = 0 | 44 | 47 | 0 | 13 | 35 | 48 | 1 | 16 | 40 | 37 | 23 |
| t = 10 min | 45 | 40 | 0 | 9 | 41 | 47 | 1 | 11 | 43 | 36 | 22 |
| t = 2 hrs | 54 | 21 | 0 | 8 | 50 | 38 | 1 | 10 | 47 | 30 | 23 |
| t = 4 hrs | 61 | 11 | 0 | 8 | 58 | 30 | 1 | 10 | 52 | 24 | 24 |
| t = 6 hrs | 67 | 6 | 0 | 8 | 63 | 25 | 1 | 10 | 56 | 20 | 24 |
| t = 24 hrs | 90 | 0 | 0 | 5 | 85 | 4 | 1 | 9 | 68 | 4 | 28 |
| pH 9, 72.5° C. | | | | | | | | | | | |
| t = 0 | 44 | 47 | 0 | 13 | 35 | 48 | 1 | 16 | 40 | 37 | 23 |
| t = 10 min | 53 | 40 | 0 | 7 | 50 | 39 | 1 | 10 | 47 | 31 | 22 |
| t = 2 hrs | 73 | 21 | 0 | 6 | 70 | 20 | 0 | 9 | 58 | 22 | 20 |
| t = 4 hrs | 83 | 11 | 0 | 6 | 80 | 10 | 0 | 9 | 67 | 14 | 19 |
| t = 6 hrs | 88 | 6 | 0 | 5 | 85 | 6 | 0 | 9 | 73 | 8 | 19 |
| t = 24 hrs | 96 | 0 | 0 | 4 | 91 | 0 | 0 | 9 | 80 | 0 | 20 |
| pH 11, 72.5° C. | | | | | | | | | | | |
| t = 0 | 44 | 47 | 0 | 13 | 35 | 48 | 1 | 16 | 40 | 37 | 23 |
| t = 10 min | 89 | 3 | 0 | 8 | 87 | 3 | 0 | 9 | 79 | 3 | 18 |
| t = 2 hrs | 94 | 0 | 0 | 6 | 90 | 0 | 0 | 10 | 81 | 0 | 19 |
| t = 4 hrs | 94 | 0 | 0 | 6 | 87 | 0 | 0 | 13 | 75 | 3 | 22 |
| t = 6 hrs | 94 | 0 | 0 | 6 | 86 | 0 | 0 | 14 | 74 | 3 | 23 |
| t = 24 hrs | 95 | 0 | 0 | 3 | 78 | 0 | 2 | 20 | 70 | 4 | 27 |

As indicated by the relative concentration decreases of the 6"-OMal and the 6"-OAc isoflavone conjugate compounds and the corresponding concentration increases of the glucosides genistin, daidzin, and glycitin, the first conversion step is most rapid and complete at higher, more basic pH conditions and higher temperatures. Substantially complete conversion of the isoflavone conjugates to isoflavone glucosides occurs in the pH 9 and pH 11 samples at both 45° C. and 72.5° C., however, daidzin and glycitin were degraded at pH 11, 11 samples at both 45° C. and 72.5° C., however, daidzin and glycitin were degraded at pH 11, 72.5° C. The conversion also proceeds to near completion in the pH 6 and 7 samples at 72.5° C. Substantial conversion of the isoflavone glucosides to aglucone isoflavones by residual enzyme in the extract occurs in the pH 6 and 7 samples at 45° C., although the conversion of the isoflavone conjugates to isoflavone glucosides is not particularly effective under these conditions.

EXAMPLE 2

In a second experiment, the conversion of isoflavone glucosides to aglucone isoflavones is examined. The extent of conversion is determined by the quantitative decrease of the percentage of the glucoside of an isoflavone family coupled with a corresponding quantitative increase of the percentage of the aglucone of the same isoflavone family.

An isoflavone glucoside enriched extract is produced from soy flakes by adjusting the pH of a soy extract to about 11 at a temperature of about 35° C. for about 1 hour. In the first samples, conversion of the isoflavone glucosides to aglucone isoflavones is effected using the residual enzyme present in an isoflavone glucoside enriched extract by adjusting the pH of the samples to pH 7.0 and pH 9.0 and holding the samples at 45° C. for 24 hours. Conversion of the isoflavone glucosides to aglucone isoflavones is effected using supplemental enzymes by dosing samples of an isoflavone glucoside enriched extract with the following commercially available supplemental enzymes: Biolactase 30,000, Quest Neutral Lactase, Lactase 50,000, Biopectinase 100L, and Alpha Gal 600. The amount of enzyme added to each sample is indicated in Table 2 below. Each sample is adjusted to a pH at which the supplemental enzyme is active, either 4.0, 4.5, or 7.0. The samples are incubated a temperatures ranging from 35° C. to 75° C. Samples are taken at selected times and measured for isoflavone content.

| Sample | GEN-ISTIN | 6"-OMAL GENISTIN | 6"-OAC GENISTIN | GEN-ISTEIN | DAID-ZIN | 6"-OMAL DIADZIN | 6"-OAC DIADZIN | DAID-ZEIN | GLYCI-TIN | 6"-OMAL GLYCITIN | GLYCI-TEIN |
|---|---|---|---|---|---|---|---|---|---|---|---|
| | | | | PERCENTAGES | | | | | | | |
| Residual enzyme pH 7.0, 45° C. | | | | | | | | | | | |
| t = 0 | 94 | 1 | 1 | 5 | 93 | 1 | 0 | 6 | 75 | 2 | 23 |
| t = 3 hrs | 94 | 1 | 1 | 5 | 93 | 1 | 0 | 6 | 75 | 2 | 22 |
| t = 6 hrs | 84 | 1 | 1 | 14 | 86 | 1 | 1 | 13 | 73 | 3 | 24 |
| t = 24 hrs | 29 | 1 | 1 | 69 | 42 | 2 | 2 | 54 | 45 | 3 | 53 |
| Residual enzyme pH 9.0, 45° C. | | | | | | | | | | | |
| t = 0 | 94 | 1 | 1 | 5 | 93 | 1 | 0 | 6 | 75 | 2 | 23 |
| t = 3 hrs | 93 | 1 | 1 | 5 | 94 | 1 | 0 | 6 | 74 | 2 | 24 |
| t = 6 hrs | 93 | 1 | 1 | 5 | 94 | 1 | 0 | 6 | 74 | 2 | 24 |
| t = 24 hrs | 0 | 1 | 0 | 99 | 1 | 1 | 4 | 93 | 18 | 5 | 77 |
| Lactase 50,000, pH 4.0, 50° C. 0.12 g/100 g extract | | | | | | | | | | | |
| t = 0 | 100 | 0 | 0 | 0 | 100 | 0 | 0 | 0 | 100 | 0 | 0 |
| t = 1 hr | 6 | 0 | 0 | 94 | 30 | 0 | 0 | 70 | 40 | 19 | 41 |
| Biolactase 30,000, pH 4.5, 35° C. 0.05 g/100 g extract | | | | | | | | | | | |
| t = 0 | 93 | 4 | 0 | 4 | 93 | 3 | 0 | 5 | 100 | 0 | 0 |
| t = 1 hr | 26 | 4 | 0 | 70 | 16 | 3 | 0 | 80 | 40 | 0 | 60 |
| t = 2 hrs | 10 | 4 | 0 | 85 | 4 | 3 | 0 | 92 | 26 | 0 | 74 |
| t = 3 hrs | 5 | 4 | 0 | 91 | 0 | 3 | 0 | 97 | 19 | 0 | 81 |
| Alpha Gal 600, pH 4.5, 75° C. 10 g/100 g extract | | | | | | | | | | | |
| t = 0 | 91 | 0 | 0 | 9 | 89 | 0 | 0 | 11 | 78 | 0 | 22 |
| t = 24 hrs | 1 | 0 | 0 | 99 | 0 | 0 | 2 | 98 | 0 | 0 | 100 |
| Biopectinase 100 L, pH 4.0, 50° C. 0.2 g/100 g extract | | | | | | | | | | | |
| t = 0 | 100 | 0 | 0 | 0 | 100 | 0 | 0 | 0 | 100 | 0 | 0 |
| t = 1 hr | 67 | 0 | 0 | 33 | 58 | 0 | 0 | 42 | 87 | 13 | 0 |
| Quest Neutral Lactase, pH 7.0, 35° C. 0.05 g/100 g extract pH 4.5 | | | | | | | | | | | |
| t = 0 | 93 | 4 | 0 | 4 | 93 | 3 | 0 | 5 | 100 | 0 | 0 |
| t = 1 hr | 66 | 4 | 0 | 30 | 66 | 3 | 0 | 31 | 77 | 0 | 23 |
| t = 2 hrs | 50 | 4 | 0 | 46 | 51 | 3 | 0 | 46 | 67 | 0 | 33 |
| t = 3 hrs | 36 | 4 | 0 | 59 | 37 | 3 | 0 | 59 | 58 | 0 | 42 |
| t = 24 hrs | 1 | 4 | 0 | 95 | 0 | 3 | 0 | 97 | 0 | 0 | 100 |

As shown by the conversion of genistin, daidzin, and glycitin to genistein, daidzein, and glycitein, respectively, substantially complete conversion of the isoflavone glucosides to aglucone isoflavones is achieved. Selected supplemental enzymes remarkably increase the rate of the conversion as compared with conversion by the residual enzyme in the extract, effecting substantially complete conversion within 1 hour at an effective concentration, temperature, and pH.

EXAMPLE 3

In another experiment, an aglucone isoflavone enriched protein material is recovered from an aglucone isoflavone enriched extract and a conventional protein material is recovered from a conventional extract. The isoflavone content in the recovered protein materials of each extract is determined at a separation pH of 4.0, 4.5, and 5.0.

An aglucone isoflavone enriched soy extract is prepared by 1) extracting defatted soy flakes with an aqueous alkaline solution; 2) adjusting the pH of the extract to 11 and holding the extract at 35° C. for 1 hour to produce an isoflavone glucoside enriched extract; and 3) adding 0.1% Lactase 50,000 (Amano International Enzyme Co.) by weight of solids in the isoflavone glucoside enriched extract to the extract, which is then treated at 50° C. and pH 4.5 for 1 hour to produce the aglucone isoflavone enriched extract. A conventional soy extract is also prepared, where the conventional extract is prepared by extracting defatted soy flakes with an aqueous alkaline solution.

A sample containing 10 g of solids is obtained from each extract, and the samples from each extract are adjusted to pH 4.5. A protein material is separated from each sample by centrifuging the sample and decanting the supernatent whey from the protein material. The isoflavone content of the separated protein material from each sample is then determined. Table 3 below shows the total isoflavone content in milligrams per sample and the percentage of each type of isoflavone of an isoflavone family present in the protein material of each of the samples.

protein material from the conventional extract contains substantial amounts of isoflavone conjugates which are absent in the aglucone isoflavone enriched protein material due to the conversion of the isoflavone conjugates to aglucone isoflavones in the aglucone isoflavone enriched extract.

In the above examples, all percentages indicated for 6"-OMal-genistin, 6"-OAc-genistin, 6"-OMal-daidzin, 6"-OAc-daidzin, glycitin, 6"-OMal-glycitin, and glycitein are calculated values. The percentages indicated or enzyme concentration are calculated from grams of commercial enzyme preparation per 100 grams solid in each sample. The following is a description of a method for quantifying isoflavones in soy products. The isoflavones are extracted from soy products by mixing 0.75 gram of sample (spray dried or finely ground powder) with 50 ml of 80/20 methanol/water solvent. The mixture is shaken for 2 hours at room temperature with an orbital shaker. After 2 hours, the remaining undissolved materials are removed by filtration through Whatman No. 42 filter paper. Five ml of the filtrate are diluted with 4 ml of water and 1 ml of methanol.

The extracted isoflavones are separated by HPLC (High Performance Liquid Chromatography)using a Hewlett Packard C18 Hypersil reverse phase column. The isoflavones are injected onto the column and eluted with a solvent gradient starting with 88% methanol, 10% water, and 2% glacial acetic acid and ending with 98% methanol and 2% glacial acetic acid. At a flow rate of 0.4 ml/min, all the isoflavones - genistin, 6"-0-acetylgenistin, 6"-0-malonylgenistin, genistein, daidzin, 6"-0-acetyldaidzin, 6"-0-malonyldaidzin, daidzin, glycitin and its derivatives and glycitein—are clearly resolved. Peak detection is by UV absorbence at 260 mm. Identification of the peaks was performed by HPLC-mass spectrometer.

Quantification is achieved by using pure standards (genistin, genistein, daidzin and daidzein) purchase from

TABLE 3

| Sample | GEN-ISTIN | 6"-OMAL GENISTIN | 6"-OAC GENISTIN | GEN-ISTEIN | DAID-ZIN | 6"-OMAL DIADZIN | 6"-OAC DIADZIN | DAID-ZEIN | GLYCI-TIN | 6"-OMAL GLYCITIN | GLYCI-TEIN |
|---|---|---|---|---|---|---|---|---|---|---|---|
| MG/SAMPLE | | | | | | | | | | | |
| Aglucone isoflavone enriched protein material, separation pH 4.5 Protein | 1.4 | 0.0 | 0.0 | 9.7 | 0.0 | 0.0 | 0.0 | 5.8 | 0.4 | 0.0 | 0.5 |
| Conventional protein material, separation pH 4.5 Protein | 1.6 | 4.3 | 0.0 | 1.6 | 0.7 | 2.3 | 0.0 | 1.2 | 0.0 | 0.4 | 0.4 |
| PERCENTAGE | | | | | | | | | | | |
| Aglucone isoflavone enriched protein material, separation pH 4.5 Protein | 13 | 0 | 0 | 87 | 0 | 0 | 0 | 100 | 49 | 0 | 51 |
| Conventional protein material, separation pH 4.5 Protein | 21 | 58 | 0 | 21 | 16 | 55 | 0 | 28 | 0 | 52 | 48 |

Comparing the isoflavone content of the protein material from the aglucone isoflavone enriched extract and the protein material from the conventional extract, it can be seen that the protein material from the aglucone isoflavone enriched extract contains significantly higher mounts of the aglucone isoflavones, particularly genistein and daidzein, than the protein material from the conventional extract. The Indofine Chemical Company, Sommerville, N.J. Response factors (integrated area/concentration) are calculated for each of the above compounds and are used to quantitate unknown samples. For the conjugated forms for which no pure standards are available, response factors are assumed to be that of the parent molecule but corrected for molecular weight difference. The response factor for glycitin is assumed to be that for genistin corrected for molecular weight difference. This method provides the quantities of each individual isoflavone. For convenience, total genistein, total daidzein and total glycitein can be calculated, and represent the aggregate weight of these compounds if all the conjugated forms are converted to their respective unconjugated forms. These totals can also be measured directly by a method using acid hydrolysis to convert the conjugated forms.

The embodiments of the invention in which an exclusive property or privilege is claimed are defined as follows.

What is claimed is:

1. A process for producing an aglucone isoflavone enriched extract from a vegetable material comprising:

extracting a vegetable material containing isoflavone conjugates and protein with an aqueous extractant having a pH above about the isoelectric point of said protein in said vegetable material;

separating said extractant from said vegetable material to form an aqueous extract containing said isoflavone conjugates and said protein;

treating said aqueous extract at a temperature of about 2° C. to about 121° C. and a pH of about 6 to about 13.5 for a time period sufficient to convert said isoflavone conjugates to isoflavone glucosides; and contacting an enzyme capable of cleaving glucoside bonds with said isoflavone glucosides in said aqueous extract at a temperate of about 5° C. to about 75° C. and a pH of about 3 to about 9 for a time period sufficient to convert said isoflavone glucosides to aglucone isoflavones.

2. The process as set forth in claim 1, wherein extraction is effected at a pH of from about 6 to about 10.

3. The process of claim 1, wherein said aqueous extract is treated at a pH value of about 9 and a temperature of about 45° C. to about 75° C. to convert said isoflavone conjugates to isoflavone glucosides.

4. The process of claim 1, wherein said aqueous extract is treated at a pH value of about 11 and a temperature of about 5° C. to about 50° C. to convert said isoflavone conjugates to isoflavone glucosides.

5. The process of claim 1, wherein contacting an enzyme with said isoflavone glucosides comprises adding an effective amount of a supplemental enzyme to said aqueous extract containing isoflavone glucosides.

6. The process of claim 5, wherein said supplemental enzyme is selected from the group consisting of alpha-galactosidase enzymes, beta-galactosidase enzymes, gluco-amylase enzymes, pectinase enzymes, and combinations thereof.

7. The process of claim 5, wherein said supplemental enzyme is added such that the total concentration of enzyme present in said aqueous extract is from about 0.1% to about 10% by weight of said vegetable material, on a dry basis.

8. The process as set forth in claim 1, wherein said vegetable material comprises a soybean material.

9. The process as set forth in claim 1, wherein a majority of said isoflavone conjugates and said isoflavone glucosides are converted to aglucone isoflavones.

10. The process as set forth in claim 1, wherein substantially all of said isoflavone conjugates and said isoflavone glucosides are converted to aglucone isoflavones.

11. The process as set forth in claim 1, further comprising adjusting the pH of said aglucone isoflavone enriched extract to about the isoelectric point of said protein to precipitate a protein material containing protein and said aglucone isoflavones.

12. The process as set forth in claim 11, wherein washing of said protein material is avoided.

13. The process as set forth in claim 11, wherein said protein material is washed with water in an mount by weight which is less than about 6 times the weight of said precipitated protein material.

14. The aglucone isoflavone enriched extract produced by the method of claim 1.

15. The aglucone isoflavone enriched protein material produced by the method of claim 11.

16. A process for producing an aglucone isoflavone enriched protein material from a vegetable material comprising:

extracting a vegetable material containing isoflavone conjugates and protein with an aqueous extractant having a pH above about the isoelectric point of said protein in said vegetable material;

separating said extractant from said vegetable material to form an aqueous extract containing said isoflavone conjugates and said protein;

treating said aqueous extract at a temperature of about 2° C. to about 121° C. and a pH of about 6 to about 13.5 for a time period sufficient to convert said isoflavone conjugates to isoflavone glucosides;

separating a protein material containing said isoflavone glucosides from said aqueous extract; and contacting said isoflavone glucosides in said protein material with an enzyme capable of cleaving glucoside bonds at a temperature of about 5° C. to about 75° C. and a pH of about 3 to about 9 for a time period sufficient to convert said isoflavone glucosides to aglucone isoflavones.

17. The process as set forth in claim 16, wherein said extraction is effected at a pH of from about 6 to about 10.

18. The process as set forth in claim 16, wherein said aqueous extract is treated at a pH of about 9 to about 11 and at a temperature of about 5° C. to about 75° C. to convert said isoflavone conjugates to said isoflavone glucosides.

19. The process as set forth in claim 16 wherein separating a protein material containing said isoflavone glucosides from said aqueous extract further comprises adjusting the pH of said aqueous extract to about the isoelectric point of said protein material to precipitate said protein material from said extract.

20. The process as set forth in claim 16 wherein contacting said isoflavone glucosides in said protein material with an enzyme comprises adding an effective amount of a supplemental enzyme to said protein material.

21. The process as set forth in claim 20 wherein said supplemental enzyme is selected from the group consisting of alpha-galactosidase enzymes, beta-galactosidase enzymes, gluco-amylase enzymes, pectinase enzymes, and combinations thereof.

22. The process as set forth in claim 20 wherein said supplemental enzyme is added to said protein material in a concentration of about 0.1% to about 10% by weight of said protein material, on a dry basis.

23. The process as set forth in claim 16, wherein said vegetable material is a soybean material.

24. The process of claim 16 wherein a majority of said isoflavone conjugates are converted to aglucone isoflavones.

25. The process of claim 16 wherein substantially all of said isoflavone conjugates are converted to aglucone isoflavones.

26. The aglucone isoflavone enriched protein material produced by the process of claim 16.

27. A process for producing an aglucone isoflavone enriched extract from a vegetable material, comprising:

forming an aqueous slurry of a vegetable material containing protein and isoflavone conjugates;

treating said aqueous slurry of said vegetable material at a temperature of about 2° C. to about 121° C. and a pH of about 6 to about 13.5 for a sufficient time to convert said isoflavone conjugates to isoflavone glucosides;

extracting said vegetable material with an aqueous extractant having a pH above about the isoelectric point of said protein in said vegetable material;

separating said extractant from said vegetable material to form an aqueous extract containing said isoflavone glucosides and said protein; and contacting said isoflavone glucosides in said aqueous extract with an enzyme capable of cleaving glucoside bonds at a temperature of about 5° C. to about 75° C. and a pH of about 3 to about 9 for a period of time sufficient to convert said isoflavone glucosides to aglucone isoflavones.

28. The process as set forth in claim 27 wherein said aqueous slurry contains up to 20% by weight of said vegetable material.

29. The process as set forth in claim 27 wherein said extraction is effected at a pH of from about 6 to about 10.

30. The process as set forth in claim 27 wherein contacting said isoflavone glucosides in said extract with an enzyme comprises adding an effective amount of a supplemental enzyme to said extract.

31. The process as set forth in claim 30 wherein said supplemental enzyme is selected from the group consisting of alpha-galactosidase enzymes, beta-galactosidase enzymes, gluco-amylase enzymes, pectinase enzymes, and combinations thereof.

32. The process as set forth in claim 30 wherein said supplemental enzyme is added to said extract in a concentration of about 0.1% to about 10% by weight of said vegetable material, on a dry basis.

33. The process as set forth in claim 27, wherein said vegetable material comprises a soybean material.

34. The process of claim 27 wherein a majority of said isoflavone conjugates are converted to said aglucone isoflavones.

35. The process of claim 27 wherein substantially all of said isoflavone conjugates are converted to aglucone isoflavones.

36. The aglucone isoflavone enriched extract produced by the process of claim 27.

37. The process as set forth in claim 27 further comprising adjusting the pH of said aglucone isoflavone enriched extract to about the isoelectric point of said protein to precipitate a protein material containing protein and said aglucone isoflavones.

38. The aglucone isoflavone enriched protein material produced by the method of claim 37.

39. A process for producing an aglucone isoflavone enriched protein material from a vegetable material, comprising:

extracting a vegetable material containing isoflavone conjugates and protein with an aqueous extractant having a pH above about the isoelectric point of said protein in said vegetable material;

separating said extractant from said vegetable material to form an extract containing said isoflavone conjugates and said protein;

separating a protein material containing said isoflavone conjugates from said extract;

forming an aqueous slurry of said protein material;

treating said aqueous slurry at a temperature of about 2° C. to about 121° C. and a pH of about 6 to about 13.5 for a period of time sufficient to convert said isoflavone conjugates to isoflavone glucosides; and contacting said isoflavone glucosides in said aqueous slurry with an enzyme capable of cleaving glucoside bonds at a temperature of about 5° C. to about 75° C. and a pH of about 3 to about 9 for a period of time sufficient to convert said isoflavone glucosides to aglucone isoflavones.

40. The process as set forth in claim 39 wherein extraction is effected at a pH of from about 6 to about 10.

41. The process as set forth in claim 39 wherein said protein material is separated from said extract by adjusting the pH of said extract to about the isoelectric point of said protein to precipitate said protein material from said extract.

42. The process as set forth in claim 39 wherein said aqueous slurry contains up to about 30% by weight of said protein material.

43. The process as set forth in claim 39 wherein said aqueous slurry is treated at a pH of about 9 to about 11 and at a temperature of about 5° C. to about 75° C. to convert said isoflavone conjugates to isoflavone glucosides.

44. The process as set forth in claim 39 wherein contacting said isoflavone glucosides in said aqueous slurry with an enzyme comprises adding an effective amount of a supplemental enzyme to said slurry.

45. The process as set forth in claim 44 wherein said supplemental enzyme is selected from the group consisting of alpha-galactosidase enzymes, beta-galactosidase enzymes, gluco-amylase enzymes, pectinase enzymes, and combinations thereof.

46. The process as set forth in claim 44 wherein said supplemental enzyme is added to said aqueous slurry in a concentration of about 0.1% to about 10% by weight of said vegetable material, on a dry basis.

47. The process as set forth in claim 39 wherein said vegetable material is comprised of a soybean material.

48. The process as set forth in claim 39 wherein a majority of said isoflavone conjugates are converted to aglucone isoflavones.

49. The process as set forth in claim 39 wherein substantially all of said isoflavone conjugates are converted to aglucone isoflavones.

50. The aglucone isoflavone enriched protein material formed by the process of claim 39.

\* \* \* \* \*